US00PP31618P3

(12) United States Plant Patent
Kleynhans

(10) Patent No.: US PP31,618 P3
(45) Date of Patent: Mar. 31, 2020

(54) ***LACHENALIA* JACQ. F. EX MURRAY PLANT NAMED 'AQUA LADY'**

(50) Latin Name: ***Lachenalia* Jacq. f. ex Murray**
Varietal Denomination: Aqua Lady

(71) Applicant: AGRICULTURAL RESEARCH COUNCIL, Pretoria (ZA)

(72) Inventor: Riana Kleynhans, Benoni (ZA)

(73) Assignee: Agricultural Research Council, Pretoria (ZA)

( * ) Notice: Subject to any disclaimer, the term of this patent is extended or adjusted under 35 U.S.C. 154(b) by 0 days.

(21) Appl. No.: 14/756,803

(22) Filed: Oct. 15, 2015

(65) Prior Publication Data

US 2017/0112037 P1 Apr. 20, 2017

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
See application file for complete search history.

(56) References Cited

PUBLICATIONS

UPOV hit on *Lachenalia* plant named 'Aqua Lady', ZA PBR ZA20104392, granted 2010.*
ARC*LNR *Lachenalia* and other Flower bulb cultivars at the ARC, R. Kleynhans and S. Venter, Jul. 2012, pp. 1-23.*
UPOV Guidelines for the conduct of tests for distinctness, homogeneity and stability. TG/126/4, published Oct. 12, 1990 downloaded from http://www.upov.int/edocs/tgdocs/en/tg126.pdf on Jan. 12, 2018. (Year: 1990).*
UPOV hit on *Lachenalia* plant named 'Aqua Lady', ZA PBR 20104392, filed Mar. 5, 2009.*
UPOV hit on *Lachenalia* plant named 'Aqua Lady', QZ PBR 42927, filed Dec. 15, 2014.*
CPVO Variety Data Sheet for Application No. 20141911, Applicant: Agrictiltural Research Council, Application/Filing Date Jul. 29, 2014, published Oct. 15, 2014 1 page, Community Plant Variety Office, France.
Certificate of Grant of Plant Breeder's Right, Registration No. ZA2010493, Applicant: ARC (Agricultural Research Council), dated Apr. 20 2010, 1 page, Department of Agrictilture Forestry and Fisheries, Republic of South Africa.
CPVO Variety Data Sheet for Application No. 20141910, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA2010492, Applicant: ARC (Agricultural Research Council), dated Apr. 20, 2010, 1 page, Department of Agriculture Forestry and Fisheries, Republic of South Africa.
CPVO Variety Data Sheet for Application No. 20141912, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104394, Applicant: ARC (Agricultural Research Council), dated Apr. 20, 2010, 1 page, Department of Agriculture Forestry and Fisheries, Republic of South Africa.
CPVO Variety Data Sheet for Application No. 20141915, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA2010496, Applicant: ARC (Agricultural Research Council), dated Apr. 20, 2010, 1 page, Department of Agriculture Forestry and Fisheries, Republic of South Africa.
CPVO Variety Data Sheet for Application No. 20141914, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104397, Applicant: ARC (Agricultural Research Council), dated Apr. 20, 2010, 1 page, Department of Agriculture Forestry and Fisheries, Republic of South Africa.
CPVO Variety Data Sheet for Application No. 20141913, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104395, Applicant: ARC (Agricultural Research Council), dated Apr. 20, 2010, 1 page, Department of Agriculture Forestry and Fisheries, Republic of South Africa.
Co-Pending U.S. Appl. No. 14/756,801, inventor Kleynhans, R., filed Oct. 15, 2015 (Not Published).
Co-Pending U.S. Appl. No. 14/756,802, inventor Kleynhans, R., filed Oct. 15, 2015 (Not Published).
Co-Pending U.S. Appl. No. 14/756,821, inventor Kleynhans, R., filed Oct. 19, 2015 (Not Published).
Co-Pending U.S. Appl. No. 14/756,819, inventor Kleynhans, R., filed Oct. 19, 2015 (Not Published).
Co-Pending U.S. Appl. No. 14/756,820, inventor Kleynhans, R., filed Oct. 19, 2015 (Not Published).
Niederwieser, J.G., and Vcelar, B., "Regeneration of *Lachenalia* Species from Leaf Explants," *HortScience* 25(6):684-687, American Society for Horticultural Science, United States (1990).

(Continued)

*Primary Examiner* — Anne Marie Grunberg
(74) *Attorney, Agent, or Firm* — Sterne, Kessler, Goldstein & Fox P.L.L.C.

(57) ABSTRACT

A new and distinct form of *Lachenalia* plant characterized by a bulb plant type having a spreading growth habit of a height of 15-30 centimetres (cm) and width of 10-15 cm having a turquoise blue flower and green leave with maroon spots, further characterized in that the spots are relatively small in size and fairly pronounced in that it has a good contrast.

2 Drawing Sheets

(56) References Cited

PUBLICATIONS

Slabbert, M.M., and Niederwieser, J.G., "In vitro bulblet production of *Lachenalia," Plant cell Reports* 18:620-624, Springer-Verlag, Germany (1999).

* cited by examiner

*LACHENALIA* JACQ. F. EX MURRAY PLANT NAMED 'AQUA LADY'

Genus and species: *Lachenalia* Jacq. f. ex Murray.
Variety denomination: 'Aqua Lady'.

BACKGROUND OF THE INVENTION

The present invention relates to a new and distinct cultivar of *Lachenalia*, botanically known as *Lachenalia* Jacq. f. ex Murray having the common name of Viooltjies/Cape cowslip and hereinafter referred to by its variety denomination 'Aqua Lady'.

The variety was first cultivated in 2008 and originated by means of conventional breeding by the inventor during 2009 to 2010 at the premises of Agricultural Research Council Vegetable and Ornamental Plant Institute, Roodeplaat, Pretoria, Republic of South Africa.

Asexual reproduction of the 'Aqua Lady' plant at the same location has shown that the unique features thereof are stable and reproduced true to type in successive generations of asexual reproduction.

SUMMARY OF THE INVENTION

The present invention constitutes a new and distinct variety of *Lachenalia* which originated from the controlled pollination between a *Lachenalia* hybrid as seed bearing parent and a *Lachenalia viridiflora* as pollen parent as detailed hereinbelow.

The following traits have been repeatedly observed and are determined to be the unique characteristics, under the local evaluation conditions, of the 'Aqua Lady' plant. These characteristics in combination distinguish 'Aqua Lady' as a new and distinct *Lachenalia* cultivar:

1. Bulb plant type having a spreading growth habit of a height of 15-30 centimetres (cm) and width of 10-15 cm.
2. Flower color: turquoise-blue (RHS #120B).
3. Leaf color: green (RHS #139B) with maroon (RHS #183A) spots.

Color references are made to The R.H.S. Colour Chart, 1$^{st}$ edition, 1966, except where general color terms of ordinary significance are used or indicated otherwise.

Plants of the new *Lachenalia* variety 'Aqua Lady' can be compared to the variety denomination 'Rupert' but differs in that the flower color of 'Aqua Lady' is turquoise-blue (RHS #120B) compared to the purple of 'Rupert'. The maroon (RHS #183A) spots of the 'Aqua Lady' plant is furthermore smaller in size, yet more pronounced in that it has a good contrast compared to the low contrast found in 'Rupert'.

'Rupert' furthermore has a shorter peduncle and more dense inflorescence compared to 'Aqua Lady'.

BRIEF DESCRIPTION OF THE DRAWINGS

The first drawing illustrates the overall appearance of the 'Aqua Lady', showing the colors as true as it is reasonably possible to obtain in colored reproductions of this type.

The first drawing comprises a front perspective view of a typical 'Aqua Lady' grown in an indoor nursery, but located in an outdoor setting.

The second drawing illustrates the overall appearance of the 'Aqua Lady', showing the colors as true as it is reasonably possible to obtain in colored reproductions of this type.

The second drawing comprises a front perspective view of a typical 'Aqua Lady' grown in an indoor nursery, but located in an outdoor setting.

DETAILED DESCRIPTION

The aforementioned drawings, following observations and measurements describe 'Aqua Lady' grown by the inventor on behalf of Agricultural Research Council Vegetable and Ornamental Plant Institute, Roodeplaat, Pretoria, Republic of South Africa. Thereafter 'Aqua Lady' was made subject of a South African Plant Breeders' Right application in March 2009. This application was granted in 2010 under number ZA20104392.

The plant is an early flowering cultivar and may be used for landscaping and should be planted during the month of March; indoors and in pots only. The plant should be kept at temperatures of 20-25 degrees Celsius during the day and 10-15 degrees Celsius at night. Plenty of light should be provided.

'Aqua Lady' is a hybrid-hybrid cross containing the following *Lachenalia* species: *Lachenalia viridiflora, Lachenalia orchioides* subsp. *glaucina, Lachenalia bulbifera, Lachenalia quadricolor* and *Lachenalia rubida.*

The female parent (GenBank accession number 1978/093/198) has flowers which are more purple with dark purple tips, but with the same flower orientation as 'Aqua Lady'.

The male parent is *L. viridiflora* (unnamed) which has blue flowers, but with much less flowers, shorter peduncle and shorter inflorescence. The leaves of this species are also shorter, with more pronounced spots as compared to those of 'Aqua Lady'.

'Aqua Lady' was originally produced sexually from a cross between the hybrid and *L. viridiflora* (unnamed) described above. A specific seedling with number 1992/125/012 was selected from this cross and thereafter asexually propagated. The asexual progeny of this seedling is the cultivar 'Aqua Lady' and was multiplied via tissue culture at the premises of Agricultural Research Council Vegetable and Ornamental Plant Institute, Roodeplaat, Pretoria, Republic of South Africa.

The following characteristics of 'Aqua Lady' are described with reference to description of said characteristic which are comparable with the mentioned variety/ies having said similar characteristic.

Leaf: Monocolored.

*Spots on upper side.*—Present, small and with good contrast.

| Characteristic: | Description of 'Aqua Lady': | Variety having similar characteristics: |
|---|---|---|
| Attitude: | Semi-erect | 'Romaud' |
| Length: | Medium - 22.5 cm | 'Bontrok', 'Winsome' |
| Width: | Medium - 4.8 cm | 'Rosabeth' |
| Ratio: length/width | Large (elongated): 4.7:1 | 'Rodelein' |
| Shape: | Oblong | 'Romargo' |
| Color: | Green (RHS #139B) | 'Roinge' |
| Leaf color designation for lower sides of the leaf | Green (RHS #139B) | |
| Shape in cross section: | Angular | 'Robyn', 'Romelia' |
| Recurving of margin: | Absent | 'Eliza', 'Rodelein' |
| Undulation of margin: | Absent | 'Romelia' |

-continued

| Characteristic: | Description of 'Aqua Lady': | Variety having similar characteristics: |
|---|---|---|
| Blistering and pubescence of upper side: | Absent | 'Rodelein', 'Rosabeth' |
| Spots on upper side: | Present (Maroon) (RHS #183A) | 'Bontrok', 'Roingec 'Rosabeth' |
| Number of spots per leaf | Amount differs from plant to plant, no exact number of spots per leaf | |
| Size of spots on upper side: | Small to medium (1-2 millimeter (mm)) | |
| Density of spots on upper side: | Medium | 'Roinge', 'Rosabeth' |
| Intensity of spots on upper side: | Dark | 'Bontrok', 'Roklara' |
| Markings on outer side of leaf base: | Present | 'Roinge', 'Rozanne' |

Peduncle:

| Characteristic: | Description of 'Aqua Lady': | Variety having similar characteristics: |
|---|---|---|
| Length: | Medium - 16.5 cm | 'Rosabeth' |
| Peduncle color designation | Maroon (RHS #183A) with green (RHS #143D) | |
| Spots or markings: | Present | 'Bontrok', Rosabeth' |
| Coloration of peduncle spots | Maroon (RHS #183A) | |
| Size of spots or markings: | Large (some cover the stem and others are between 0.1-1 cm) | 'Roinge', Rolina' |
| Density of spots or markings: | Dense, close to each other: spots may be as close as 0.2 mm, but may differ | 'Roinge' |

Bud:

| Characteristic: | Description of 'Aqua Lady': |
|---|---|
| Color | Turquois (RHS #121 C) with green (RHS #143D) tip |

Inflorescense:

| Characteristic: | Description of 'Aqua Lady': | Variety having similar characteristics: |
|---|---|---|
| Length: | Medium - 13 cm | 'Robyn', 'Roklara' |
| Rudimentary apex: | Conspicuous | 'Ronette' |
| Number of flowers: | Few (20-30 flowers) | 'Bontrok' |

Flower:

| Characteristic: | Description of 'Aqua Lady': | Variety having similar characteristics: |
|---|---|---|
| Description of floral organs | Inflorescence containing individual tubular flowers attached with pedicels to the peduncle | |

-continued

| Characteristic: | Description of 'Aqua Lady': | Variety having similar characteristics: |
|---|---|---|
| Attitude: | Horizontal | 'Robyn', Romargo' |
| Pedicel: | Present | 'Romelia' |
| Length of pedicel: | Medium (2-3 mm) | 'Bontrok', 'Louis' |
| Length of flower: | Medium - 2.8 cm | 'Lizelle', 'Rolane', 'Sonni' |
| Diameter excluding apex: | Medium - 0.8 cm | 'Romargo', 'Romelia', 'Rosabeth' |
| Diameter at apex: | Medium - 1.0 cm | 'Ronita' |
| Attitude of distal part of inner perianth segments | Straight | 'Robyn' |
| Glossiness: | Absent | |
| Predominant color: | Turquoise-blue (RHS #120B) | 'Ronita' |
| Intensity of predominant color: | Medium | 'Gail' |
| Outer perianth segment: color of basal part just before opening of flower | Blue-green (RHS #121A of RHS color chart, 2nd edition, 1986) | |
| Outer perianth segment: color of basal part of fully opened flower | Blue-green (RHS #121A of RHS color chart, 2nd edition, 1986) | |
| Outer perianth segment: color of apex relative to other part | Clearly different | 'Ronette' |
| Outer perianth segment: color of apex if clearly different from other part | Turquoise-blue (RHS #120B) | 'Gail', 'Robyn' |
| Inner perianth segment: distinct spot in middle of apex | Present | 'Ronette' |
| Inner perianth segment: color of margin of apex relative to other part | Clearly different | 'Louis', Roinge' |
| Inner perianth segment: color of differently colored margin of apex | Purple (RHS #81B) | 'Leipoldt', 'Louis' |
| Inner perianth segment: predominant color of exposed part (excluding differently colored margin of apex) | Blue-green (RHS #121A of RHS color chart, 2nd edition, 1986) | |
| Length of inner perianth segment compared to outer segments: | Longer | 'Roinge', Rosabeth' |
| Extrusion of stamens: | Absent | 'Roinge', Rosabeth' |
| Fragrance: | Absent | 'Romelia' |
| Bulb: predominant shape: | Oblate | 'Romaud' |
| Time of flowering: | Early - flowering time vary from April to May (Southern Hemisphere) | 'Celia', 'Lizelle', 'Sonni' |
| Duration of flowering: | Medium (Up to 1 and half to 2 months) | 'Rodelein', Roinge' |

Others:

| Characteristic: | Description of 'Aqua Lady': |
|---|---|
| Description of the bulb including size and color of the bulb at maturity | Cream/white (color designation - RHS #158C) Size: between 1.5 to 2 cm in diameter |
| Time of leaf growth/bud burst | Starts within the first week of watering (normally March/April in Southern Hemisphere) |
| A description of any fruit and seed set | No seed or fruit |
| Timing of leaf senescence | After flowering has completed and starts to die down, the leaves start to die off (wheat color) and plant dry out (September-October in Southern Hemisphere) |

The variety is not genetically modified and has been tested to be free of Ornithogalum Mosaic Virus.

The invention claimed is:

1. A new and distinct variety of *Lachenalia* plant named 'Aqua Lady' as illustrated and described herein.

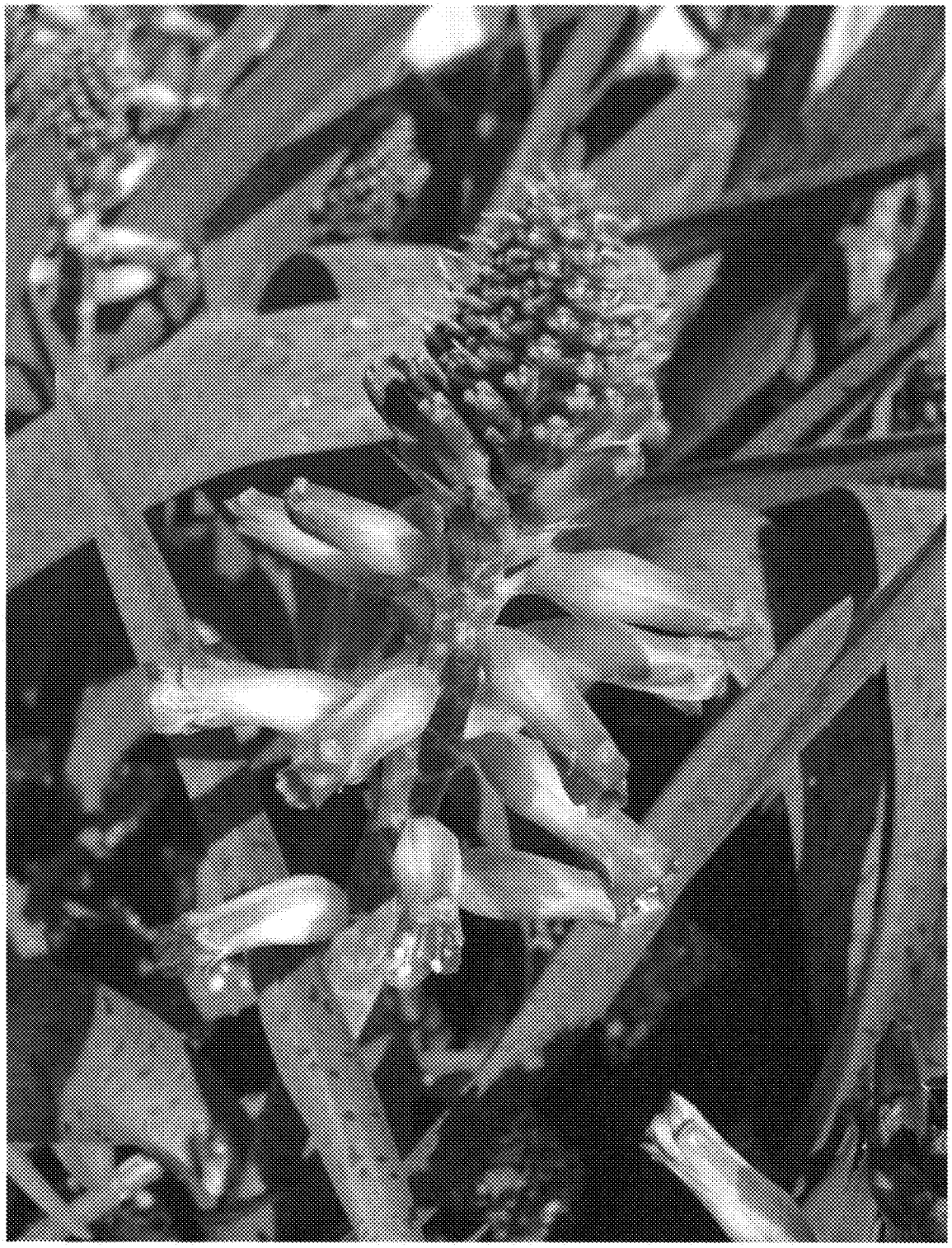

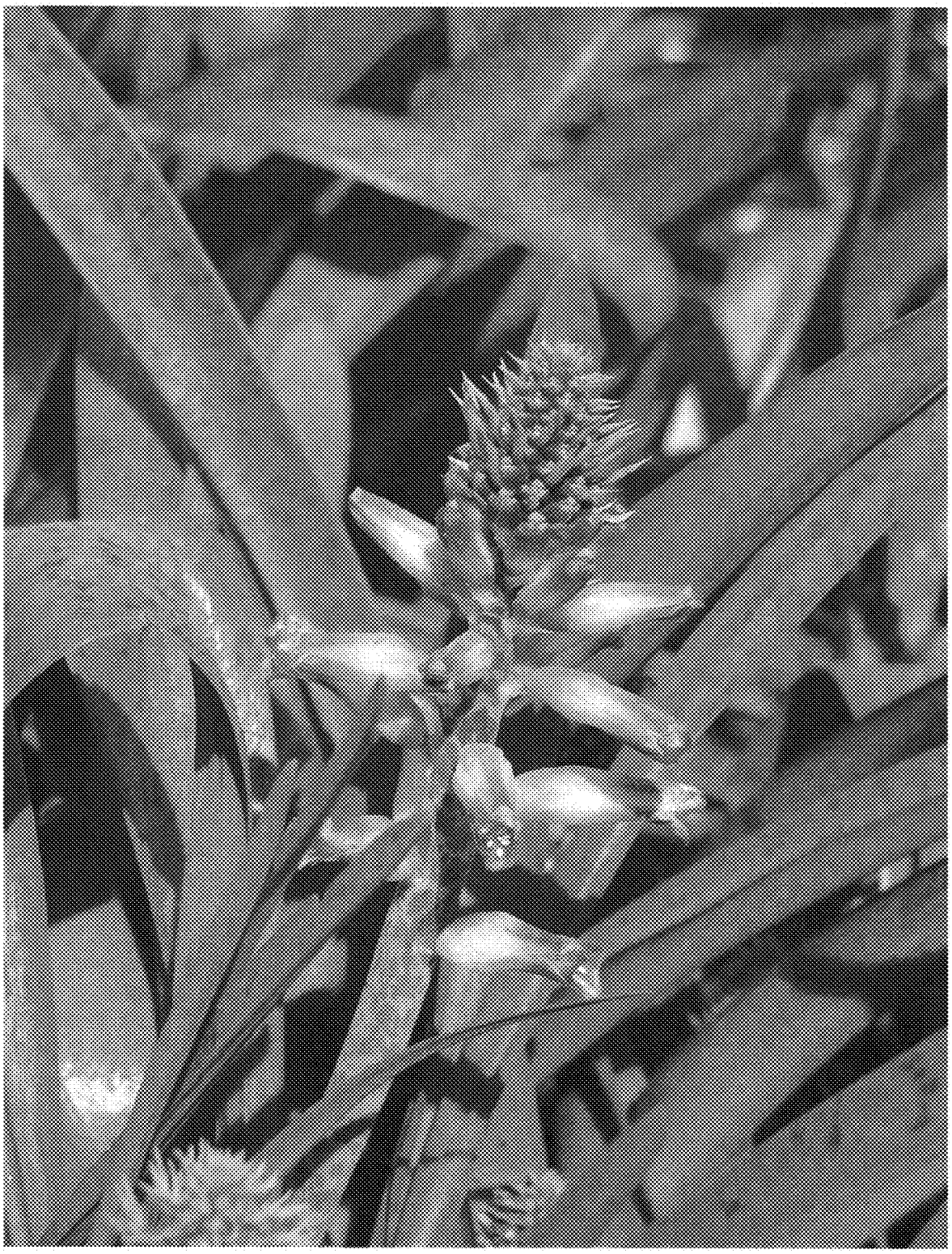

* * * * *